United States Patent [19]

Kambara et al.

[11] Patent Number: 4,879,012
[45] Date of Patent: Nov. 7, 1989

[54] METHOD FOR REUTILIZATION OF ELECTROPHORESIS GEL

[75] Inventors: Hideki Kambara, Hachioji; Tetsuo Nishikawa, Koganei, both of Japan

[73] Assignee: Hitachi, Ltd., Tokyo, Japan

[21] Appl. No.: 211,284

[22] Filed: Jun. 24, 1988

[30] Foreign Application Priority Data

Jun. 24, 1987 [JP] Japan ................ 62-155447

[51] Int. Cl.⁴ ............................. G01N 27/26
[52] U.S. Cl. ..................... 204/157.15; 204/180.1; 204/182.8; 204/299 R
[58] Field of Search ............... 204/182.8, 182.9, 180.1, 204/299 R, 157.15

[56] References Cited

U.S. PATENT DOCUMENTS 4,675,300 6/1987 Zare et al. ............... 204/180.1
4,729,947 3/1988 Middendorf et al. ....... 204/180.8

OTHER PUBLICATIONS

Smith, Lloyd M. et al, "Fluorescence Detection in Automated DNA Sequence Analysis", Nature, vol. 321 (Jun. 12, 1986), pp. 674-679.

Peck, K. and Morris M. D., "Sensitive Photothermal Densitometer for Quantitation of Coomassie Brilliant Blue Stained Proteins in Polyacrylamide Gels", Analytical Chemistry, 1986, 58, pp. 506-507.

Primary Examiner—John F. Niebling
Assistant Examiner—John S. Starsiak, Jr.
Attorney, Agent, or Firm—Antonelli, Terry & Wands

[57] ABSTRACT

An electrophoresis gel is regenerated by light-irradiating an electrophoresis gel used for separating a fluorescence-labeled sample by electrophoresis and optically detecting the sample, thereby photo-dissociating a fluorescence-labeling substance remaining in the electrophoresis gel and reutilizing the resulting gel repeatedly. A troublesome operation of preparing an electrophoresis gel at every occasion of separation and detection can be saved thereby.

7 Claims, 2 Drawing Sheets

METHOD FOR REUTILIZATION OF ELECTROPHORESIS GEL

BACKGROUND OF THE INVENTION

This invention relates to a method for reutilizing an electrophoresis gel for fluorescence-labeled DNA, RNA or protein separation.

Heretofore, gel electrophoresis has been used for the separation of DNA, etc, and the detection is made with radioisotope labeled of fluorescence-labeled DNA, etc. [see, for example, Japanese Patent Application Kokai (Laid-open) No. 61-62843]. In this case, once the separation and detection are made, the labeled sample remains in the electrophoresis gel, which cannot be repeatedly used. That is, an electrophorosis gel must be prepared at every occasion of separation and detection.

Recently, a disposable gel in which the gel is supported on a film has been commercially available for radioisotope-labeled samples, whereby the operation to prepare a gel can be saved. However, the disposable gel cannot be used for detection with light, because, when the gel is irradiated with light to observe a fluorescence, a strong fluorescence is emitted from the film member itself and interferes with the fluorescence emitted from the fluorescence-labeled DNA, thereby making the fluorescence from the fluorescence-labeled DNA less observable.

It seems that the DNA or RNA sequencing method or the protein detection method will be shifted from the conventional radioisotope labeling procedure to the fluorescence labeling procedure. However, neither development of a disposable gel suitable for the fluorescence labeling procedure nor regeneration and reutilization of the gel has been proposed yet, and the gel must be prepared at every occasion of separation and detection. This has required a troublesome operation.

SUMMARY OF THE INVENTION

An object of the present invention is to provide a method for regenerating and reutilizing an electrophoresis gel, where a gel, once prepared, can be repeatedly reutilized while saving an operation of preparing a gel at every occasion of separation and detection, based on the fluorescence labeling.

This object can be attained by using an easily photodissociatable substance as a fluorophore and irradiating fluorescence-labeled DNA, etc. remaining in the gel with light after the detection, thereby degenerating the fluorophore into a substance incapable of emitting the fluorescence.

Generally, fluorophores, when irradiated with light, emit fluorescence through excitation and undergo photo-dissociation at the same time. Susceptibility to the photo-dissociation depends upon the species of fluorophores, and there are easily photo-dissociable fluorophores such as fluroesin isothiocyanate (FITC; excitation wave length: 494 nm; emission wave length: 511 nm). When DNA, etc. are labeled with such an easily photodissociable fluorophore and subjected to separation and detection by gel electrophoresis, the fluorescence-labeled sample remaining in the gel after the detection undergoes decomposition upon irradiation with a strong light and no more emits the fluorescence. Though DNA, etc. still remain in the gel, they are no more detectable with light, and thus the gel can be reutilized in the separation and detection.

PREFERRED EMBODIMENTS OF THE INVENTION

Figure 1:
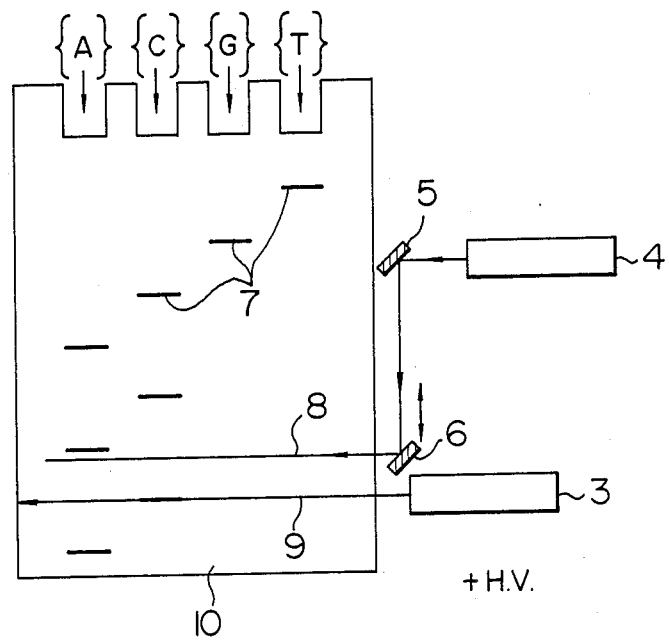
FIG. 1 is a schematic view of one embodiment according to the present invention.
Figure 2:
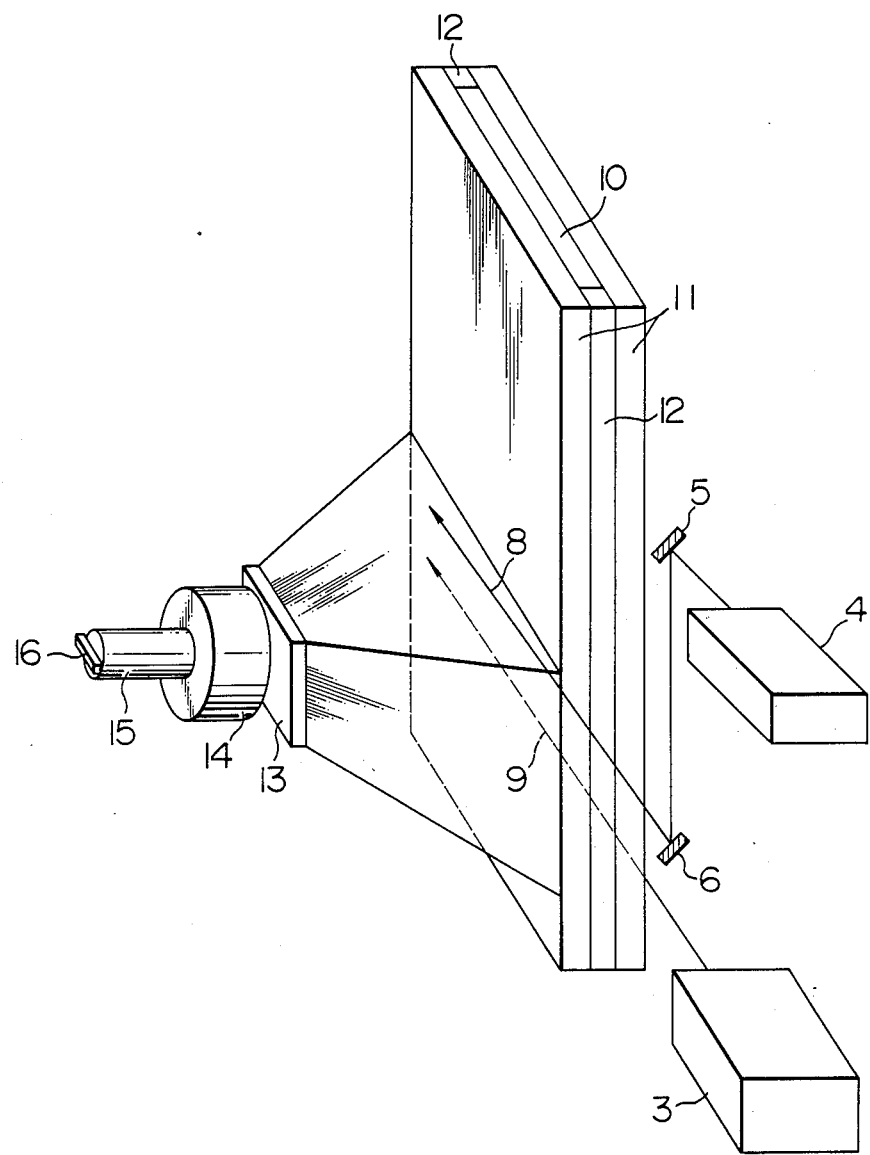
FIG. 2 is a perspective view of the embodiment shown in FIG. 1.

One embodiment of the present invention will be described in detail below, referring to FIGS. 1 and 2, where fluorescence-labeled DNA sequencing is carried out.

Four kinds of fragments {A}, {T}, {C}and {G}, each labeled with FITC at one end and terminated with adenine (A), thymine (T), cytosine (C) and guanine (G) at other ends, respectively, are subjected to migration along the individual tracks of an electrophoresis gel plate 10, which is sandwiched with quartz plates 11 for supporting the gel and provided with spacers 12 at both side ends. A detection region at a predetermined level distant from the starpoint of migration is irradiated with a laser beam 9 generated from a generator 3 for exciting fluorophores, and the fluorescence emitted from fluorescence-labeled DNA 7 passing through the detection region is led to a photodiode array 16 through a filter 13, a focusing lens 14 and an image intensifier 15. The shorter the DNA, the faster the DNA migrates. Thus, the base number can be determined from the emission time and the base species can be determined from the track identification. Thus, the sequence can be determined from the base number and the base species. An argon laser (488 nm) with 10 mW is used as an exciting light source 3 for determining the sequence. The migration is carried out usually for 5 to 6 hours and the sequence up to 300-base DNA can be determined. Fluorescence-labeled along DNAs remain between the startpoint of migration and the light-irradiated detection region after the end of measurement, which is a great trouble for detecting next samples, because overlapping of signals from the residual previous samples and the new samples occurs. To overcome this trouble, an argon laser (488 nm) with about 1 W from a laser source 4 for photo-dissociating the fluorophore remaining in the gel after the measurement is focused onto an area with a diameter of about 1 mm and introduced into the gel plate 10 as a laser beam 8 from the side of the gel plate 10 through a reflection mirror 5 and a moving mirror 6, and FITC is decomposed by irradiating the gel plate 10 with the laser beam 8 while moving the moving mirror 6 to make scanning throughout the gel plate 10. The thus treated electrophoresis gel plate 10 can be reutilized. However, this application has limits to the dissociation cross-section ($\sigma$) of the labeling substance and the laser intensity.

These limits have been investigated.

Actually determined dissociation cross-section ($\sigma$) of FITC is as follows:

$$\sigma = \text{about } 0.5 \times 10^{-20} \text{ cm}^2.$$

The dissociation cross-selection ($\sigma$) can be defined by the following equation:

$$-dC = C \cdot \sigma \cdot p dt$$

where
  C: concentration of fluorophore dC: dissociation rate of fluorophote per unit time
ρ: photon density By solving the equation, the following equation can be obtained.

$$C = C_0 e^{-\sigma \rho t}$$

where
$C_o$: concentration at t=0

$t = (\sigma \cdot \rho)^{-1}$: time by which the concentration reaches $e^{-1}$ and which corresponds to an average life.

When an argon laser with 1 W is focused onto an area of 1 mm², the photon density ρ will be about $2.5 \times 10^{19}$ photons/mm².sec. It can be seen from the dissociation cross-section σ and the photon density ρ that the time by which the concentration of FITC reaches $e^{-1}$, that is, the average life, is about 0.1 second. In order to dissociate the fluorophore to such a degree that the concentration of the fluorophore can be disregarded, the irradiation must be carried out for about 0.5 seconds per length of 1 mm. With irradiation for 0.5 seconds, the concentration can be decreased to $e^{-5} \simeq 6 \times 10^{-3}$.

The residual FITC-labeled samples are distributed over the entire migration tracks, but it is not necessary to dissociate the samples throughout the entire migration tracks. Actually, it is satisfactory to dissociate the fluorophores remaining between the startpoint of migration and the laser-irradiated detection region. If the distance therebetween is 200 mm, and if the laser beam scanning is made at a rate of 2 mm/sec, the scanning time is 100 seconds. When a low cost light source of 100 mW class is used as a laser source, the scanning time will be 1,000 seconds, which is about 20 minutes. The scanning time for the dissociation must be one hour at longest. If the scanning time is more than one hour, it is better to prepare a new gel plate, because it can be prepared faster than such a long scanning time. In the light of these situations, the selection standard for the laser power for the scanning irradiation is at least about 40 mW. The smaller the dissociation cross-section (6), the longer the scanning time. Thus, the lower limit to the dissociation cross-section is about $10^{-22}$ cm², where scanning irradiation for the dissociation with a laser with 1 W requires 20 seconds per length of 1 mm and thus about one hour is required until the dissociation has been completed.

On the other hand, too large a dissociation cross-section is inconvenient. Fluorescence-emitting cross-section is usually in an range of about $10^{-16}$ cm², and flurorphores with a dissociation cross-section of $10^{-20}$ cm² emit $10^4$ fluorescences on average until they have been dissociated. The larger the dissociation cross-section, the smaller the amount of fluorescences to be emitted. Thus, no higher sensitivity can be obtained. The time required for a DNA band to pass through the irradiated region, 0.5 mm wide, under the ordinary DNA separation and detection conditions is 20 to 30 seconds. Even if 50% of the fluorophore in the DNA band is dissociated during the passage through the irradiated region, there is no trouble at all for the detection. Since an argon laser with 5-10 mW is focused to a cross-section of about 0.5 mm² and used for the detection, the photon density will be about $2-5 \times 10^7$ photons/mm².sec. At a photon density of $1 \times 10^{17}$ photons/mm².sec., the fluorophore with a dissociation cross-section of $10^{10}$ cm² will be dissociated for about one second, and a larger dissociation cross-section than $10^{-19}$ cm² is not preferable.

When a fluoroscence-labeled compound with a dissociation cross-section of $10^{-19}$ to $10^{-22}$ cm² is used, fluorescence detection with a high sensitivity and gel utilization by photo-dissociation can be carried out.

Light irradiation can be carried out by sweeping line irradiation, entire surface irradiation with a lamp, etc.

As described above, a fluorescence-labeled compound remaining in a migration gel plate after the detection of the behavior of the electrophoresis separation through the emitted fluorescence is photo-dissociated and the resulting gel plate can be reutilized according to the present invention.

What is claimed is:

1. A method for reutilizing an electrophoresis gel which comprises irradiating an electrophoresis gel used for electrophoresis separation of a fluorophore-labeled sample and detection of the fluorescene emitted from the sample separated by electrophoresis with light, thereby photo-dissociating the fluorophore remaining in the gel and utilizing the irradiated gel; the fluorophore having a dissociation cross-section of $10^{-22}$ to $10^{-19}$ cm² and being FITC and said electrophoresis gel being irradiated with an argon laser with 40 mW or more, focused onto an area of 1 mm² as the light and the electrophoresis gel being scanned with said argon laser, thereby dissociating the fluorophore.

2. A method of regenerating an electrophoresis gel which has been used for electrophoresis separation of a fluorophore-labeled sample, said electrophoresis gel having a startpoint of migration of said sample and a detection region in which the fluorescence emitted from the sample is detected, which comprises a light irradiation step for irradiating substantially an entire area of said electrophoresis gel existing between said startpoint of migration and said detection region with light, thereby photodissociating the fluorophore remaining in the gel existing in said area.

3. A method according to claim 2, wherein a substance having a dissociation cross-section of $10^{-22}$ to $10^{-19}$ cm² is used as the fluorophore.

4. A method according to claim 3, wherein the substance is FITC.

5. A method according to claim 4, wherein an argon laser with 40 mW or more, focused onto an area of 1 mm² is used as the light and the electrophoresis gel is scanned with said argon laser over all of said area.

6. A method for electrophoresis combined with light detection, which comprises a detection step of introducing a fluorophore-labeled sample into a gel from a startpoint of migration, separating said fluorophore-labeled sample in said gel by electrophoresis, irradiating the gel in a predetermined detection region apart from said startpoint of migration with an exciting light beam and detecting fluorescence emitted from the sample passing through said predetermined detection region, and a gel regeneration step of irradiating substantially an entire area of the gel existing between said startpoint of migration and said detection region with light after completion of the detection step, thereby photo-dissociating the fluorophore remaining in said area.

7. An apparatus for electrophoresis combined with light detection, which comprises an gel plate for separating a fluorophore-labeled sample by electrophoresis, a first light irradiation means for irradiating a detection region of said gel plate with a first light beam, thereby emitting a fluorescence from the sample passing through said detection region, a detection means for detecting the fluorescence emitted from the sample, and a second light irradiation means for irradiating substantially an entire area of the gel plate existing between a startpoint of migration of the sample and said detection region with a second light beam, thereby photo-dissociating the fluorophore remaining in said area.

* * * * *